United States Patent [19]

Nachbur et al.

[11] 4,178,398
[45] Dec. 11, 1979

[54] AMIDOPHOSPHATE REACTION PRODUCTS USED AS FLAMEPROOFING AGENTS

[75] Inventors: Hermann Nachbur, Dornach; Peter Rohringer, Basel, both of Switzerland

[73] Assignee: Ciba-Geigy Corporation, Ardsley, N.Y.

[21] Appl. No.: 890,780

[22] Filed: Mar. 23, 1978

Related U.S. Application Data

[62] Division of Ser. No. 684,988, May 10, 1976, Pat. No. 4,094,929.

[30] Foreign Application Priority Data

May 15, 1975 [CH] Switzerland .................... 6264/75

[51] Int. Cl.$^2$ ................... C07F 9/24; C09K 3/28
[52] U.S. Cl. ................... 427/379; 106/18.17; 252/8.1; 427/301; 427/390 D; 428/921; 260/926; 260/968
[58] Field of Search ............ 260/926, 968; 427/394, 427/390 D, 379, 381; 428/921; 106/15 FP; 252/8.1

[56] References Cited

U.S. PATENT DOCUMENTS

| | | | |
|---|---|---|---|
| 2,574,515 | 11/1951 | Walter et al. | 260/926 |
| 2,574,517 | 11/1951 | Walter et al. | 260/926 |
| 3,597,503 | 8/1971 | Wilson et al. | 260/937 |
| 3,767,736 | 10/1973 | Bucke | 260/950 |
| 3,795,613 | 3/1974 | Hotten | 252/49.9 |
| 4,055,689 | 10/1977 | Nachbur et al. | 427/390 D |
| 4,094,929 | 6/1978 | Nachbur et al. | 260/968 |

*Primary Examiner*—John D. Smith
*Attorney, Agent, or Firm*—Prabodh I. Almaula

[57] ABSTRACT

Reaction products containing at least two amidophosphate radicals are disclosed. They have been produced from
(1) an amidophosphate of the formula

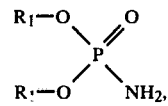

wherein $R_1$ is lower alkyl or both $R_1$'s together are lower alkylene,
(2) formaldehyde,
(3) optionally an aliphatic diol with 2 to 6 carbon atoms,
(4) optionally a lower alkanol.

If a diol according to (3) has been used, $R_1$ in the amidophosphate according to (1) can also be lower alkenyl or halogenoalkyl.

The disclosed reaction products are suitable for flameproofing organic fibre materials, especially cellulosic textiles.

12 Claims, No Drawings

AMIDOPHOSPHATE REACTION PRODUCTS USED AS FLAMEPROOFING AGENTS

This is a division of application Ser. No. 684,988 filed on May 10, 1976, now U.S. Pat. No. 4,094,929, issued June 13, 1978.

The invention relates to reaction products containing at least two amidophosphate radicals per molecule, which reaction products have been produced from
(1) at least one amidophosphate of the formula

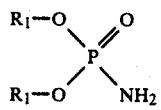

wherein $R_1$ represents alkyl having 1 to 3 carbon atoms, or both $R_1$'s together represent alkylene having 2 to 5 carbon atoms,
(2) formaldehyde or an agent releasing formaldehyde,
(3) optionally at least one aliphatic diol having 2 to 6 carbon atoms,
(4) optionally at least one alkanol having 1 to 3 carbon atoms,
whereby, provided that the constituent (3) has been concomitantly used, $R_1$ in the employed amidophosphate of the formula (1) can additionally represent alkenyl or halogenoalkyl having 2 or 3 carbon atoms.

The amidophosphate reaction products contain as a rule radicals of one and the same compound of the formula (1). It is however also possible for the reaction products to contain radicals of more than one compound of the formula (1). That is to say, the amidophosphate reaction products can be synthesised from compounds of the formula (1) which differ from each other.

The radicals $R_1$ in the formula (1) can represent, for example, n-propyl, isopropyl, methyl or, in particular, ethyl.

Furthermore, both $R_1$'s together can represent branched-chain or straight-chain alkylene, such as ethylene, n-propylene, 1-methyl-n-propylene or 2,2-dimethyl-propylene.

In addition, provided that the constituent (3) has been used, $R_1$ can additionally represent 2-chloroethyl, 2-bromoethyl, 2,3-dichloropropyl, preferably allyl or, in particular, 2,3-dibromopropyl.

The compounds of the following formulae may be given as examples of compounds usable as constituent (1):

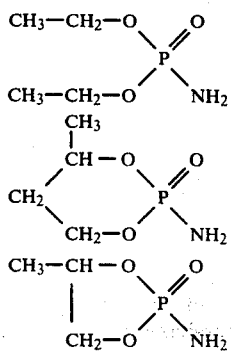

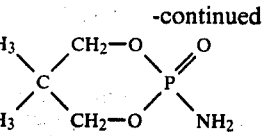

or, provided that the constituent (3) has been used, additionally the compounds of the formulae

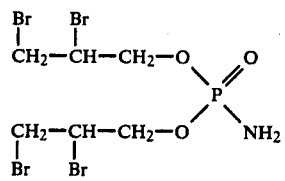

or

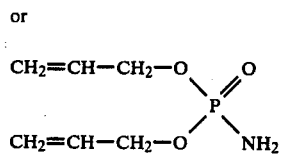

The compounds preferred are those corresponding to one of the formulae (2.5), (2.6), preferably (2.4) or especially (2.1).

The amidophosphates used as constituent (1) are known per se, or they can be produced by known methods, e.g. by the action of ammonia gas in organic solutions of the corresponding phosphates in the presence of carbon tetrachloride.

The constituent (2) is preferably formaldehyde itself, especially in the form of an aqueous formaldehyde solution, but it can also be an agent releasing formaldehyde, for example trioxane, or preferably paraformaldehyde.

In the case where the constituent (3) is used, the amidophosphate reaction products contain as a rule radicals of one and the same constituent (3). It is however also possible for the reaction products to contain radicals of more than one compound of the formula (3); that is to say, the amidophosphate reaction products can optionally be synthesised from diols differing from each other as constituent (3).

The optionally employed constituent (3) consists of aliphatic diols having 2 to 6 carbon atoms, which diols preferably correspond to the formula $$HO-Q_1-OH \qquad (3)$$

wherein $Q_1$ represents an alkylene group having at most 6 carbon atoms, which group is optionally halogenated and optionally includes 1 or 2 oxygen atoms or 1 or 2 double or triple bonds in the chain system; and particularly to the formula $$HO-Q_2-OH \qquad (4)$$

wherein $Q_2$ represents an alkylene group having at most 6 carbon atoms, which group is optionally substituted with 2 to 4 chlorine or bromine atoms and optionally includes 1 or 2 oxygen atoms or a double or triple bond in the chain system, whereby 2 or 3 carbon atoms are present between the oxygen atoms.

Examples of such diols are: ethylene glycol, diethylene glycol, triethylene glycol, 1,2-propylene glycol, dipropylene glycol, butanediol-1,4, pentanediol-1,5, neopentyl glycol, hexanediol-1,6, hexanediol-2,5, butene-2-diol-1,4, butene-3-diol-1,2, butine-2-diol-1,4 and hexine-3-diol-2,5.

Instead of the last-mentioned ethylenic or acetylenic unsaturated aliphatic diols, the corresponding halogenated, preferably chlorinated, and especially brominated, compounds can advantageously be used, such as butane-dibromo-2,3-diol-1,4, butane-dibromo-3,4-diol-1,2, butane-tetrabromo-2,2,3,3-diol-1,4, 2,2-bis-bromomethylpropanediol-1,3 and hexane-tetrabromo-3,3,4,4-diol-2,5.

Diethylene glycol, 1,2-propanediol, 2,3-dibromobutane-1,4-diol and, in particular, ethylene glycol are especially preferred.

The constituent (4) is preferably not concomitantly used. If necessary, however, the products which are advantageously used are those of which the free methylol groups are etherified. A suitable etherification constituent (4) is in this case, for example, isopropanol, n-propanol, preferably ethanol or, in particular, methanol.

The phosphorus-containing reaction products according to the invention do not as a rule have a homogeneous structure, but in most cases contain various proportions of higher and lower condensation products.

$Q_1$ represents an alkylene group having at most 6 carbon atoms, which is optionally halogenated and optionally includes 1 or 2 oxygen atoms or 1 or 2 double or triple bonds in the chain system, and $Y_1$ represents hydrogen or alkyl having 1 to 3 carbon atoms, and wherein s, t, t', x and y are each 1 or 2, whereby the sum (X+y) is 2 or 3, and, provided that s is 2, $R_1$, $R'_1$ and $R''_1$ can each additionally represent alkenyl or halogenoalkyl having 2 or 3 carbon atoms.

Of particular value are also amidophosphate reaction products of the probable formula

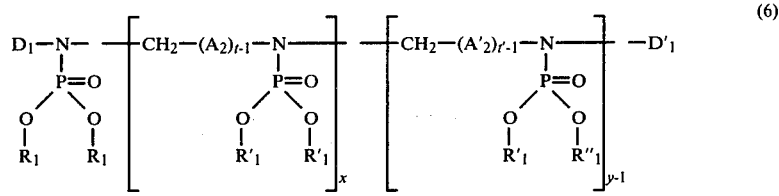

(6)

wherein $A_2$ and $A'_2$ each represent $-(O-Q_2)_{s-1}-O-CH_2-$ and $Q_2$ represents an alkyl group having at most 6 carbon atoms, which is optionally substituted with 2 to 4 chlorine or bromine atoms and which optionally includes 1 or 2 oxygen atoms or a double or triple bond in the chain system, whereby 2 or 3 carbon atoms are present between the oxygen atoms, and $D_1$, $D'_1$, $R_1$, $R'_1$, $R''_1$, s, t, t', x and y have the given meanings.

Especially suitable, however, are amidophosphate reaction products of the probable formula

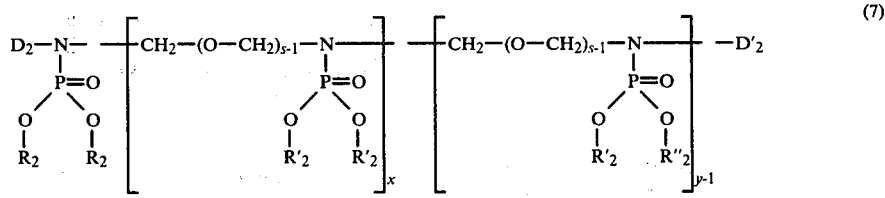

(7)

wherein $D_2$ or $D'_2$ each represent hydrogen or $-CH_2-O-Y_2$, $R_2$, $R'_2$ and $R''_2$ each represent alkyl having 1 to 3 carbon atoms, or both $R_2$'s, both $R'_2$'s The average molecular weight of the reaction products is generally between 260 and 2400.

Preferred amidophosphate reaction products correspond probably to the formula

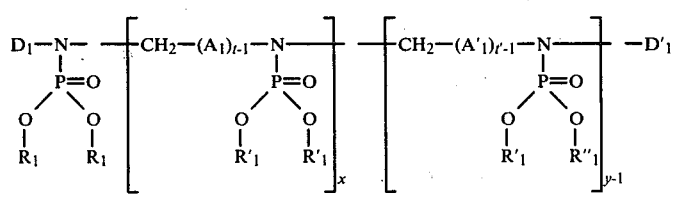

(5)

wherein $A_1$ and $A'_1$ each represent $-(O-Q_1)_{s-1}-O-CH_2-$, $D_1$ and $D'_1$ each represent hydrogen or $-CH_2-O-Y_1$, $R_1$, $R'_1$ and $R''_1$ each represent alkyl having 1 to 3 carbon atoms, or both $R_1$'s, both $R'_1$'s or both $R''_1$'s together represent alkylene having 2 to 5 carbon atoms, or both $R''_2$'s together represent alkylene having 2 to 5 carbon atoms, $Y_2$ represents hydrogen, methyl or ethyl, and wherein s, x and y are each 1 or 2, whereby the sum (x+y) is 2 or 3.

Products which have proved particularly advantageous are the phosphorus-containing reaction products of the probable formulae

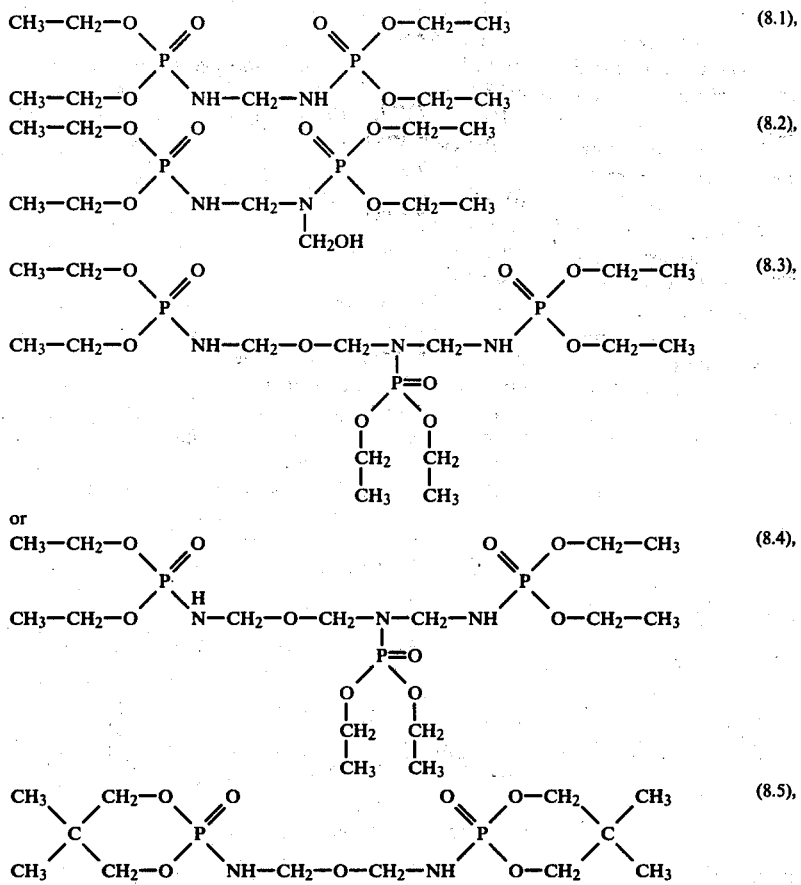

or, provided that the constituent (3) has been used, of the probable formula

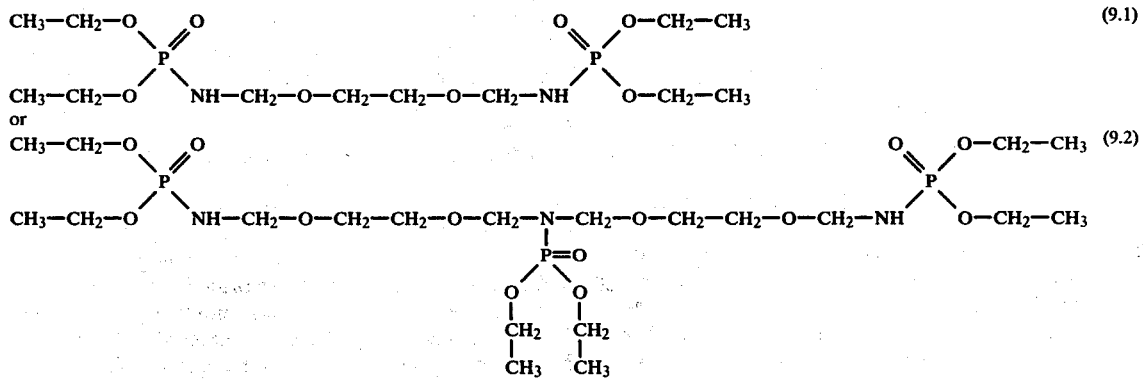

The amidophosphate groups in the formulae (5) to (7) substituted with R are attached with a methylene carbon atom, which originates from formaldehyde, to a nitrogen atom of a further dialkylamidophosphate group, or with an —O—CH$_2$ group to a nitrogen atom of a further dialkylamidophosphate group which is methylolated, whereby the —O—CH$_2$ group originates from the methylol group of the methylolated dialkylamidophosphate group.

If the constituent (3) has been used, the amidophosphate groups substituted with R are attached with a methylene carbon atom, originating from formaldehyde, by way of an -O-alkylene group, originating from the diol, and an —O—CH$_2$-group to a nitrogen atom of a further dialkylamidophosphate group which is methylolated, whereby the —O—CH$_2$-group originates from the methylol group of the methylolated dialkylamidophosphate.

Depending on what value x and y in the formulae (5) to (7) have, the reaction products concerned will have either 2 or 3 amidophosphate groups and 0 to 2 methylol groups, which can optionally be partially or completely etherified.

The amidophosphate reaction products according to the invention can be produced by customary methods known per se. They are produced advantageously by a process wherein 1 or 2 moles of the constituent (1) is reacted with 1 mole of the constituent (2); the reaction products thus obtained are optionally after-methylolated with the constituent (2); or optionally etherified with the constituent (3) and thereupon optionally after-methylolated with the constituent (2); and the after-methylolated products are optionally after-etherified with the consituent (4).

The reaction with the constituent (2) or the after-methylolation with the constituent (2) is performed advantageously at 20° to 80° C., preferably at 20° C. or at 50° to 60° C. Particularly at 50° to 60° C. this reaction is optionally performed in the presence of a basic catalyst, whereby both strong bases, such as sodium hydroxide or potassium hydroxide, and weak bases, such as sodium acetate, magnesium carbonate or magnesium oxide, can be used. There is performed in particular the reaction of 2 moles of the constituent (1) with 1 mole of the constituent (2), preferably at 20° C. without catalyst, whereby 1 mole of an amidophosphate reaction product containing 2 amidophosphate groups is obtained.

It is possible by determination of the bound formaldehyde to establish the degree of methylolation during the course of the reaction.

In a preferred process, the amidophosphate reaction products of the invention are produced by firstly methylolating 1 mole of the constituent (1) with 1 mole of the constituent (2), and subsequently condensing the resulting product at 20° to 120° C., optionally in the presence of at least one inert organic solvent insoluble in water, and optionally with the concomitant use of an acid catalyst.

The methylolated amidophosphate firstly obtained condenses with itself to form amidophosphates containing two or three amidophosphate groups. This condensation reaction is preferably performed at 50° to 80° C. It can however be performed also at 20° C., e.g. in a preferably aqueous application bath.

As a rule, the acid catalyst is optionally used in the reaction performed without the use of solvent, i.e. where the reaction is carried out in an aqueous medium. Suitable acid catalysts are strong inorganic acids, such as phosphoric acid, hydrochloric acid or sulphuric acid; also inorganic salts having an acid action, e.g. magnesium chloride, iron-III-chloride, zinc nitrate or, in particular, strong organic acids, such as p.-toluenesulphonic acid, or especially phthalic acid.

Suitable organic inert solvents or solvent mixtures which can be optionally concomitantly used are, in particularly, such solvents which are immiscible with water and which form with water an azeotrope. Especially suitable are aromatic hydrocarbons such as benzene, toluene, o-, m-, p-xylene or a mixture thereof; also xylene/toluene, xylene/benzene or xylene/decahydronaphthalene mixtures. With the use of such solvents, the reaction is as a rule performed at the boiling point of the solvent or solvent mixture, whereby the water formed by the reaction is removed azeotropically from the reaction mixture.

The etherification with the constituent (3), optionally to be performed, is advantageously carried out at 20° to 80° C., especially at 50° to 60° C., in the presence of an acid catalyst. Suitable acid catalysts are the same inorganic acids, inorganic salts and organic acids as those mentioned in the foregoing.

After-etherified amidophosphate reaction products can be optionally obtained by complete or partial etherification of the methylol groups with the constituent (4), with this etherification, optionally to be performed, being carried out at 20° to 80° C., preferably at 50° to 60° C., in an acid medium.

The amidophosphate reaction products are suitable, in particular, as effective and permanent flameproofing agents for organic fibre materials, especially for cellulose-containing fibre materials, whereby the cellulose or the cellulose constituent of the fibre material comes, e.g., from linen, artificial silk, spun rayon, or preferably from regenerated cellulose, e.g. viscose or especially cotton. Also suitable besides pure cellulose fibres are fibre mixtures such as polyacrylonitrile/cellulose, polyamide/cellulose or, in particular, polyester/cellulose. The fibre materials concerned are, for example: wood, paper or preferably textiles in any desired stage of processing, such as filaments, yarns, spools, fleeces, knitwear, fabrics or finished articles of clothing.

The amidophosphate reaction products which have been produced with the concomitant use of the constituent (3) and which contain chlorine atoms and especially bromine atoms are suitable however also as flameproofing agents for fully-synthetic fibre materials, e.g. polyacrylonitrile, acrylonitrile mixed polymers, polyamide and particularly polyester.

In the case of the acrylonitrile mixed polymers, the acrylonitrile proportion is advantageously at least 50 percent by weight and preferably at least 85 percent by weight of the mixed polymer. They are in particular mixed polymers for the production of which there are used other vinyl compounds as co-monomers, such as vinyl chloride, vinylidene chloride, methyl acrylates, acrylamide or styrenesulphonic acids.

Suitable polyamide fibres are, for example, those from poly-2-caprolactam, polyhexylmethylenediamineadipate or poly-ω-aminoundecanoic acid.

The preferred polyester fibres are derived in particular from terephthalic acid, e.g. from poly(ethylene glycol terephthalate) or poly(1,4-cyclohexylenedimethyleneterephthalate). Polyester fibres are described, for example, in the U.S. Pat. Nos. 2,465,319 or 2,901,446.

The invention hence relates also to a process for the flameproofing of fibre materials.

For the flameproofing of fully-synthetic fibre materials with halogenated, especially brominated, amidophosphate reaction products, these products are incorporated, e.g., into the spinning solutions of polyacrylonitrile, acrylonitrile mixed polymers, polyamides or in particular polyesters.

Halogenated amidophosphate reaction products are preferably applied, however, as organic solutions or, in particular, as aqueous solutions, emulsions or suspensions to the fully-synthetic fibre materials, whereupon the fibre material is dried and subjected to a heat treatment at 175° to 220° C., preferably 190° to 210° C.

Suitable organic solvents for this purpose are aliphatic alcohols, ketones or esters having at most 4 carbon atoms, aromatic or cycloaliphatic hydrocarbons or chlorinated aliphatic hydrocarbons having 1 to 7 carbon atoms. Of particular value are ethanol, methanol and trichloroethylene.

To the aqueous emulsions or suspensions there can be added the dispersing agents customary in the dye and textile industry, such as lignin sulphonates, aromatic sulphonic acids, saturated-aliphatic dicarboxylic acids substituted with longer alkyl groups, condensation products from aromatic sulphonamides and formaldehyde, alkylphenol-ethyleneoxy adducts, fatty acid, fatty amine or fatty alcohol ethyleneoxy adducts, sulphated substituted benzimidazoles or sulphonated fatty acid amides.

The fibre materials preferably rendered flameproof with the amidophosphate reaction products are however especially fibre materials containing cellulose, whereby there are applied to these fibre materials at least one amidophosphate reaction product and, optionally, a polyfunctional compound containing oxygen and/or nitrogen; the material is thereupon dried and subjected to a treatment at elevated temperature.

The amidophosphate reaction products and the polyfunctional compound are advantageously applied in the form of an aqueous preparation. The pH of the aqueous preparations is as a rule 5.0 to 7.5 and especially 6.0 to 7.0. In the case of pH-values of 5.0 to 6.0, the reaction of the amidophosphate with methylolated, polyfunctional compounds, particularly with aminoplast pre-condensates, can be performed, as already mentioned, in situ, i.e. in the aqueous preparation, immediately before application thereof to the fibre materials. If necessary, the preparations can be adjusted with inorganic acids, such as hydrochloric acid, sulphuric acid or preferably phosphoric acid, or with inorganic bases such as an aqueous potassium-hydroxide or, in particular, sodium-hydroxide solution, to the preferred pH-value of 6.0 to 7.0.

$H_2$—CO—NH—$CH_2OH$. Compounds preferably used are the methylol compounds of a urea, of an ethyleneurea or, in particular, of melamine. Valuable products are yielded in general by compounds methylolated to the highest possible degree, but particularly also by low-methylolated compounds, e.g. etherified or unetherified methylolmelamines such as di- or trimethylolmelamine, or their corresponding ethers. Suitable aminoplast pre-condensates are both principally monomolecular aminoplasts and higher pre-condensed aminoplasts.

Also the ethers of these aminoplasts pre-condensates can be used together with the amidophosphate reaction products. For example, the ethers of alkanols such as of methanol, ethanol, n-propanol, isopropanol, n-butanol or pentanols are advantageous. It is advantageous, however, if these aminoplast pre-condensates are water-soluble, such as pentamethylolmelaminedimethyl ether or trimethylolmelaminedimethyl ether.

To be mentioned as a further, in some cases advantageous, additive is a softening finishing agent, e.g. an aqueous polysiloxane emulsion or polyethylene emulsion or ethylene-copolymer emulsion, or especially soft-handle agents such as are described in the Belgian Pat. No. 808,621, e.g. the imidazole of the formula

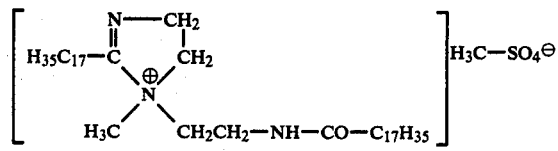

(10)

An addition of buffer substances, such as sodium bicarbonate, di- and trisodium phosphate or triethanolamine, can also be advantageous.

For acceleration of curing, the preparations can also contain so-called latently acid catalysts such as ammonium chloride, ammonium dihydrogen-orthophosphate, magnesium chloride, zinc nitrate and others, especially 2-amino-2-methyl-1-propanol hydrochloride.

In addition to containing the amidophosphate reaction products and, optionally, the additives required for adjustment of the pH-value, and the latently acid catalysts, the preparations for flameproofing advantageously also contain at least one polyfunctional oxygen-containing and/or nitrogen-containing compound for the attainment of a flameproofing finish fast to washing. Such compounds are, for example, polyfunctional epoxides, particularly epoxides liquid at 20° C. containing at least two epoxide groups, which are derived preferably from polyvalent phenols; polyalkylenepolyamines; or especially aminoplast pre-condensates.

Aminoplast pre-condensates are as a rule addition products of formaldehyde with methylolatable nitrogen compounds. The following may be mentioned as methylolatable nitrogen compounds: 1,3,5-aminotriazines such as n-substituted melamines, e.g. N-butylamine, N-trihalogenomethylmelamines, triazones as well as guanamines, e.g. benzoguanamines, acetoguanamines or diguanamines.

Also suitable are: cyanamide, acrylamide, alkyl- or arylurea and -thioureas, alkyleneureas or -diureas, e.g. urea, thiourea, urones, ethyleneurea, propyleneurea, acetylenediurea or, in particular, 4,5-dihydroxyimidazolidone-2 and derivatives thereof, e.g. the 4,5-dhydroxyimidazolidone-2 substituted in the 4-position on the hydroxyl group with the group —$CH_2C$- or highly etherified melamine-formaldehyde condensation products modified with fatty acid alkanolamides.

Also the addition of wetting agents, such as of condensation products from alkylated phenols with ethylene oxide, can be advantageous.

The content of amidophosphate reaction products in the aqueous preparations is advantageously such that 10 to 28% is applied to the material to be treated. In this connection it is to be taken into account that the commercial textile materials made from untreated or regenerated cellulose are able to absorb between 50 and 120% of an aqueous preparation.

The amount of the additive used to bring the pH-value to 6.0 to 7.0 is dependent on the value selected and on the nature of the additive.

If there are introduced into the preparation further additives, such as a latently acid catalyst, a softening agent and/or a wetting agent of the given type, then this is done advantageously in small amounts, e.g. 1 to 10%, relative to the amount of the phosphorus-containing reaction product.

In a preferred embodiment, the aqueous preparations for flameproofing cellulose-containing fibre materials contain 100 to 400 g/l, preferably 150 to 300 g/l, of at least one amidophosphate reaction product according to the invention, 50 to 300 g/l, preferably 100 to 200 g/l, of at least one polyfunctional compound, especially of an aminoplast pre-condensate, and 0 to 80 g/l, preferably 2 to 40 g/l, of at least one of the aforementioned additives.

The preparations are subsequently applied to the cellulose-containing fibre materials, which can be effected in a manner known per se. Piece-goods are preferably treated and these are impregnated on a padding machine of the usual design, which is charged with the preparation at room temperature.

The fibre material impregnated in this manner has then to be dried, which is advantageously performed at a temperature of up to 100° C. The material is afterwards subjected to a dry heat treatment at temperatures of above 100° C., e.g. between 130° and 200° C. and preferably between 150° and 180° C., the duration of which can be shorter the higher the temperature is. The duration of heating is, for example, 2 to 6 minutes at temperatures of 150° to 180° C.

In the case where amidophosphate reaction products which have been methylolated and, optionally, after-etherified are used, there occurs in the heating process the splitting of the methylol groups or, optionally, of the methylol ether groups, so that water or, optionally, an alcohol is formed.

It has been shown in this case that these volatile cleavage products have to be continuously removed from the material, so that the desired action can occur to the full extent. The apparatus in which the heat treatment is carried out is to be selected accordingly. The apparatus which is well suited is that into which, with maintenance of the prescribed temperature, fresh air can be continuously fed and from which the air laden with the formed volatile substances can be removed.

Such apparatus, e.g. so-called turbofixers or nozzle fixers, is known.

A subsequent scouring with an acid-binding agent, preferably with aqueous sodium carbonate solution, e.g. at 40° C. to boiling temperature, during 3 to 10 minutes is advantageous in the case of a strongly acid reaction medium.

The flameproof finishes obtained by the present process have, as already indicated, the advantage that they are largely retained even after repeated washing or dry-cleaning. This applies also in the case of small deposits, i.e. with small amounts of phosphorus on the finished material.

Furthermore, the flameproof finishes obtained result in no unacceptable deterioration of the textile-mechanical properties of the material treated. This is especially true with regard to the handle of the finished textile material. In particular, the tear strength of the finished textile material is to a great extent retaine even after a chlorine treatment with a hypochlorite solution, whereby the materials bleached with chlorine are subsequently subjected to a heat treatment. In addition, the finished textiles remain fast to shrinking evn after repeated washing.

A further advantage of the amidophosphate reaction products is that in the process of flameproofing fibre materials with these reaction products the treated material does not turn yellow. Particularly advantageous is also the good stability over several hours of the aqueous preparations containing the amidophosphate reaction product of the invention, which are used in the process.

Except where otherwise stated, percentages and parts in the following Examples are units of weight. Parts by volume are to parts by weight as ml to g.

MANUFACTURING INSTRUCTIONS FOR INTERMEDIATE PRODUCTS

A. 612 parts of diethylamidophosphate (4 moles) and 367 parts of a 36% aqueous formaldehyde solution (4.4 moles) are dissolved at 20° C., and the pH-value is adjusted to 10 to 11 by the addition of in all 8.2 parts of a 30% aqueous sodium hydroxide solution. Methylolation is performed for 3 hours at 20° to 30° C. at pH 10 to 11. An approximately 90% methylolation is ascertained by determining the content of free formaldehyde in a reaction specimen. The water is thereupon removed from the reaction mixture at 50° C. under vacuum.

There are obtained as methylolation product 725 parts (99% of theory) of a yellowish viscous liquid. The methylolated product corresponds to the probable formula

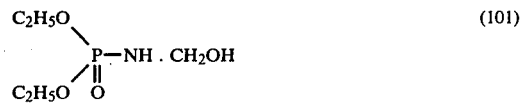

(101)

B. 165 parts of neopentylamidophosphate (1 mole) and 90.4 parts of a 36.5% aqueous formaldehyde solution (1.1 moles) are dissolved at 20° C., and the pH-value is brought to 8.5 to 9.0 by the addition in all of 23 parts of a 30% aqueous sodium hydroxide solution. Methylolation is performed for 15 minutes at 60° C. at pH 8.5 to 9.0. An approximately 83% methylolation is ascertained by determining the content of free formaldehyde in a reaction specimen. The water is thereupon removed from the reaction mixture at 60° C. under vacuum.

There are obtained as methylolation product 195 parts (99% of theory) of a white viscous syrup. The methylolated product corresponds to the probable formula

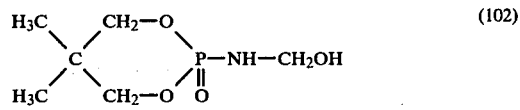

(102)

EXAMPLE 1

153 parts (1 mole) of diethylamidophosphate are dissolved in 41.6 parts of a 36% aqueous formaldehyde solution (0.5 mole), and the solution is allowed to stand for 48 hours at 20° C. The water of the formaldehyde solution as well as the water formed during the reaction is thereupon removed at 60° C. in vacuo. There are obtained 159 parts (~100% of theory) of a colourless semi-solid product. This contains as chief constituent a compound corresponding to the probable formula

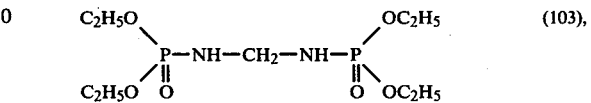

(103), which is confirmed by the following elementary analysis:

Calculated: C=33.97%; H=7.6%; N=8.8%; P=19.47%. Found: C=32.3%; H=7.8%; N=8.6%; P=18.8%.

Gel permeation chromatography (GPC) shows the following composition:

approx. 17% of a reaction product having a molecular weight of about 650 and 4 phosphorus atoms,
approx. 19% of a reaction product having a molecular weight of about 480 and 3 phosphorus atoms,
approx. 45% of a reaction product having a molecular weight of about 320 and 2 phosphorus atoms, and
approx. 19% of diethylamidophosphate.

EXAMPLE 2

79.5 parts (0.25 mole) of the compound described in Example 1 are dissolved in 20.8 parts (0.25 mole) of a 36% aqueous formaldehyde solution at 20° C. The pH-value of the solution is adjusted to 10 to 10.5 by the addition of a 30% aqueous sodium hydroxide solution, whereby the temperature rises temporarily to about 40° C. The solution is subsequently cooled again to 20° C., and at this temperature it is held for a further 3 hours at pH 9.5 to 10.5 by the occasional addition of sodium hydroxide solution. For the maintenance of the pH value, there are required altogether 7.7 parts of the 30% aqueous sodium hydroxide solution. The examination of a specimen of the reaction mixture to determine its content of free formaldehyde shows that now 94% of the employed formaldehyde is bound. There are obtained as methylolated reaction product 105 parts of an opalclouded viscous solution which has a phosphorus content of 13.8% and a content of active substance of 80.5%.

The resulting product contains as main constituent a compound corresponding to the probable formula $$\begin{array}{c} C_2H_5O \\ \diagdown \\ C_2H_5O \diagup \underset{O}{\overset{\|}{P}} - N - CH_2 - NH - \underset{O}{\overset{\|}{P}} \diagdown OC_2H_5 \\ \phantom{C_2H_5O \diagup P - }CH_2OH \phantom{-NH-P\diagdown} OC_2H_5 \end{array}$$ (104), which is confirmed by the following elementary analysis:

Calculated: C=34.5%; H=7.53%; N=8.04%; P=17.8%. Found: C=33.4%; H=7.5%; N=7.9%; P=17.5%.

EXAMPLE 3

183 parts (1 mole) of the intermediate product obtained according to the manufacturing instruction A and 160 parts of benzene are heated to the boiling temperature (78° C.). The water formed by etherification is removed azeotropically and collected separately. The reaction is finished after about 5 hours, with altogether 8 parts of water having been separated. The benzene is removed from the reaction mixture under vacuum at about 50° to 60° C.

There are obtained as residue 176 parts of a viscous, slightly yellowish liquid consisting of a mixture of at least two reaction products which correspond to the two probable formulae:

$$\begin{array}{c} C_2H_5O \diagdown \phantom{xxxxxxxxxxxxxxxxx} OC_2H_5 \\ P-NH-CH_2-O-CH_2-NH-P \\ C_2H_5O \diagup \overset{\|}{O} \phantom{xxxxxxxxxxxx} \overset{\|}{O} \diagdown OC_2H_5 \end{array}$$ (105)

$$\begin{array}{c} C_2H_5O \diagdown \phantom{xxxxxxxxxxxxxxxxxxxxxxxxxxx} OC_2H_5 \\ P-NH-CH_2-O-CH_2-N-CH_2OCH_2-HN-P \\ C_2H_5O \diagup \overset{\|}{O} \phantom{xxxxxxxxx} \underset{P=O}{|} \phantom{xxxxxxxxxx} \overset{\|}{O} \diagdown OC_2H_5 \\ \phantom{xxxxxxxxxxxxxxxx} O \diagup \phantom{x} \diagdown O \\ \phantom{xxxxxxxxxxxxxxxx} | \phantom{xxxxx} | \\ \phantom{xxxxxxxxxxxxxxxx} H_5C_2 \phantom{xxx} C_2H_5 \end{array}$$ (106).

The formulae (105) and (106) are confirmed by the following elementary analysis:

calculated for formula (105): C=34.7%; H=7.5%; N=7.9%; P=17.0%:

calculated for formula (106): C=35.36%; H=7.42%; N=7.73%; P=17.1%.

For the mixture of formulae (105) and (106) there is found: C=34.5%; H=7.53%; N=8.04%; P=17.8%.

The separation of the resulting mixture by means of GPC shows the following composition:

approx. 2% of a reaction product having a molecular weight of about 740 and 4 phosphorus atoms, approx. 6% of a reaction product having a molecular weight of about 320 and 4 phosphorus atoms, approx. 15% of a reaction product having a molecular weight of about 540 and 3 phosphorus atoms, approx. 37% of a reaction product having a molecular weight of about 350 and 2 phosphorus atoms, approx. 15% of a reaction product having a molecular weight of about 210 and 1 phosphorus atom, approx. 19% of a reaction product having a molecular weight of about 180 and 1 phosphorus atom, and approx. 6% of diethylamidophosphate.

EXAMPLE 4

183 parts (1 mole) of the intermediate product obtained according to the manufacturing instruction A are etherified in the presence of 5 parts of phthalic acid for 3 hours at 50° C. The reaction mixture is thereupon cooled to 20° C. and neutralised with 8 parts of a 30% aqueous sodium hydroxide solution to pH 6.5 to 7.0, and the formed fine suspension is poured into 200 parts of acetone. After the precipitated sodium phthalate has been filtered off, the filtrate is freed from acetone and water in vacuo at about 50° C.

There are obtained 172 parts of a colourless clear liquid consisting of a mixture of at least two of the reaction products given in Example 3.

The probable formulae (105) and (106) are confirmed by the following elementary analysis:

calculated for formula (105): C=34.7%; H=7.5%; N=7.9%; P=17.0%;

calculated for formula (106): C=35.36%; H=7.42%; N=7.73%; P=17.1%.

Found for the mixture of formula (105) and (106): C=34.3%; H=7.6%; N=7.8%; P=17.0%.

The separation of the resulting mixture by means of GPC shows the following composition:

approx. 8% of a reaction product having a molecular weight of about 740 and 4 phosphorus atoms, approx. 6% of a reaction product having a molecular weight of about 320 and 4 phosphorus atoms, approx. 18% of a reaction product having a molecular weight of about 540 and 3 phosphorus atoms, approx. 38% of a reaction product having a molecular weight of about 350 and 2 phosphorus atoms, approx. 14% of a reaction product having a molecular weight of about 210 and 1 phosphorus atom, approx. 9% of a reaction having a molecular weight of about 180 and 1 phosphorus atom, and approx. 7% of diethylamidophosphate.

EXAMPLE 5

69.6 parts (0.2 mole) of the compounds obtained according to Example 3 are dissolved in 16.6 parts of a 36% aqueous formaldehyde solution (0.2 mole) at 20° C. The solution is adjusted by the addition of a 30% aqueous sodium hydroxide solution, with stirring, to pH 10.0 to 10.5, and methylolated for 3 hours at 20° to 30° C., with the pH being maintained at 10.0 to 10.5 by the occasional addition of sodium hydroxide solution. Altogether there are required 7 parts of the sodium hydroxide solution. By testing of a specimen of the reaction mixture for its content of free formaldehyde, there is ascertained a 69-70% methylolation, which cannot be increased even by a further 3 hours' treatment.

There are obtained as methylolated reaction product 88.5 parts of a colourless clear viscous solution which has a phosphorus content of 14.0 and a content of active substance of 85.4%.

The resulting product consists of a mixture of at least two compounds which correspond to the partially methylolated form of the two probable formulae in Example 3.

EXAMPLE 6

183 parts (1 mole) of the product obtained according to manufacturing instruction A and 31 parts of ethylene glycol (0.5 mole) are etherified in the presence of 5 parts of phthalic acid for 3 hours at 50° to 55° C. The reaction mixture is thereupon cooled to 20° C. and is neutralised with 8 parts of a 30% aqueous sodium hydroxide solution to pH 6.5 to 7; and the formed fine suspension is poured into 120 parts of acetone. After the precipitated sodium phthalate has been filtered off, the acetone and water are removed from the filtrate in vacuo at about 50° C.

There are obtained 199 parts of a colourless clear, low-viscous liquid consisting of a mixture of at least two reaction products which correspond to the two following probable formulae:

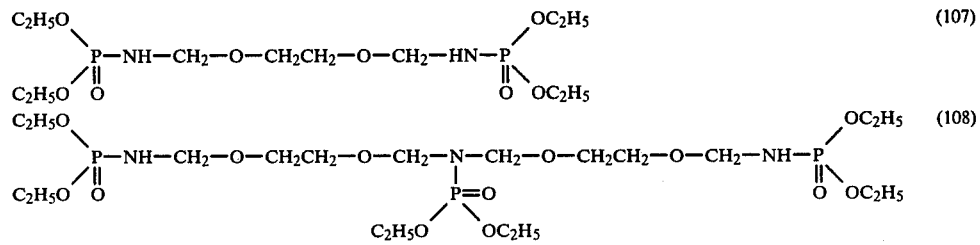

The formulae (107) and (108) are confirmed by the following elementary analysis:

calculated for formula (107): C=36.74%; H=7.71%; N=7.14%; P=15.8%;

calculated for formula (108): C=38.04%; H=7.66%; N=6.65%; P=14.7%;

found for the mixture of formula (107) and (108): C=36.3%; H=7.8%; N=6.9%; P=15.0%.

EXAMPLE 7

175 parts (1 mole) of the intermediate product obtained according to manufacturing instruction B are etherified in the presence of 5 parts of phthalic acid for 3 hours at 50° to 60° C. The reaction mixture is thereupon cooled to 20° C. and neutralised with 8.5 parts of a 30% aqueous sodium hydroxide solution to pH 6.5 to 7.0; and the viscous reaction mixture is diluted with 500 parts of acetone. The resulting fine suspension is filtered off from the precipitated sodium phthalate, and the filtrate is freed from acetone and water in vacuo at about 50° C.

There are obtained, as a colourless brittle substance that is hard at 20° C., 156 parts of a product containing as the main constituent a compound corresponding to the probable formula

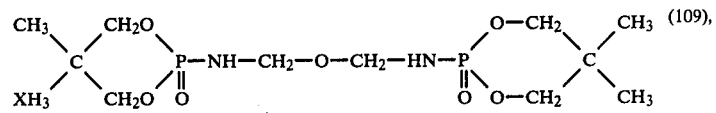

which is confirmed by the following elementary analysis:

Calculated: C=38.7%; H=7.05%; N=7.5%; P=16.65%, Found: C=40.0%; H=7.2%; N=7.0%; P=14.8%.

The following Table 1 shows the absorption bands of the infra-red absorption spectra of the reaction-product mixtures obtained according to the Examples Nos. 1 to 7.

w = weak absorption,
m = medium absorption, and
s = strong absorption.

Table 1

| cm$^{-1}$ | 1 | 2 | 3 | 4 | 5 | 6 | 7 |
|---|---|---|---|---|---|---|---|
| 3690 m | | | | | | | x |
| 3630 w | x | x | x | x | x | x | |
| 3690 m | | | | | | | x |
| 3530 w | x | x | x | x | x | x | |
| 3520 m | x | x | | x | | x | |
| 3400 m-s | | x | | | x | | x |
| 3360 m | x | x | x | x | | x | |
| 3320 s | | x | | x | | x | |
| 3020 w | x | x | x | x | x | x | |
| 2960 s | x | x | x | x | x | x | x |
| 2860 m | x | x | x | x | x | x | x |
| 2850 m | x | x | x | x | x | x | x |
| 2830 m | x | x | x | x | x | x | x |
| 2590 w | | | x | x | | x | x |
| 1530 w | x | x | | x | | x | |
| 1495 w | x | x | | x | | x | |
| 1460 w-m | x | x | x | x | x | x | x |
| 1430 w | x | x | x | x | x | x | x |
| 1405 w | x | x | x | x | x | | |
| 1380 w-m | x | x | x | x | | x | x |
| 1360 m | x | x | x | x | x | x | x |

Table 1-continued

| cm$^{-1}$ | Example No. | | | | | | |
|---|---|---|---|---|---|---|---|
| | 1 | 2 | 3 | 4 | 5 | 6 | 7 |
| 1315 w | | | x | x | x | | |
| 1280 w-m | x | x | x | x | x | x | x |
| 1230 s | x | x | x | x | x | x | x |
| 1180 s | x | x | x | x | x | x | x |
| 1150 w-m | x | x | x | x | x | x | |
| 1115 m | | | | | | | x |
| 1080 s | x | x | x | x | x | x | x |
| 1040 s | x | x | x | x | x | x | x |
| 1010 s | x | x | x | x | x | x | |
| 995 s | | | | | | | x |
| 960 m-s | x | x | x | x | x | x | x |
| 940 m | | x | | x | | | x |
| 920 w | x | x | x | x | x | x | x |
| 905 w | | | | | | x | x |
| 870 s | | | x | | | x | x |
| 860 w | x | x | | x | x | x | |
| 840 w | x | x | x | x | x | x | |
| 815 w | x | x | x | x | x | x | x |

EXAMPLE 8

A cotton fabric (weight per unit area: 150 g/m$^2$) is padded with the aqueous liquor A of the composition given in the following Table 2. The liquor absorption is 80%. The material is dried for 30 minutes at 80° C. and curing is then performed for 4½ minutes at 160° C. A portion of the fabric is subsequently washed at 95° C. for 5 minutes in a solution containing per litre of water 4 g of anhydrous sodium carbonate and 1 g of a reaction product from 1 mole of 4-nonylphenol and 9 moles of ethylene oxide; the material is afterwards rinsed and dried.

A further portion of this fabric is now washed up to 40 times in the course of 60 minutes in a solution at 95° C. containing per litre 5 g of household detergent according to SNV 198,861.

The individual fabric samples are then tested for their flameproofness (Vertical Test according to DIN 53906). The results of this test are likewise summarised in the following Table 2.

Furthermore, the handle of the fabric is examined after subsequent washing and assessed on the basis of handle ratings according to the following scale.

0=unchanged; 1=slightly stiffer than 0; 2=somewhat stiffer than 0; 3=stiff; and 4=very stiff.

Table 2

| | Untreated | Treated with liquor A |
|---|---|---|
| constituents in g/l | | |
| product according to Example 1 (P-content: 19.5%) | | 160 |
| di-trimethylolmelamine | | 150 |
| reaction product from 1 mole of 4-nonylphenol and 9 moles of ethylene oxide | | 2 |
| 2-amino-2-methyl-1-propanol-hydrochloride | | 40 |
| hexamethylolmelaminepentamethyl ether-stearic acid-alkanolamide reaction product 30% | | 20 |
| g P/kg of fabric | | 25 |
| pH value of the bath | | 5.6 |
| fixation degree in % | | 70 |
| flameproofness | | |
| BT = burning time in sec. | | |
| TL = tear length in cm. | | |
| after subsequent washing BT | burns | 0 |
| TL | | 10.5 |
| after 20 washes BT | burns | 0 |
| TL | | 12.5 |
| after 40 washes BT | burns | 0 |
| TL | | 13.5 |
| handle | 0 | 1 |

EXAMPLE 9

In a manner analogous to that described in Example 8, a cotton fabric is flameproofed with the liquors A to E of the composition given in the following Table 3 and subsequently tested.

Besides the assessment of the handle, there is also carried out the Scorch Test according to AATCC 92-1967, in which the damage caused by retained chlorine is estimated. For this purpose the fabrics are treated with a sodium hypochlorite solution and then rinsed. A portion of the fabric is afterwards heated locally in the warp-direction on a heating plate. The tear strength of the fabrics treated with chlorine on the one hand and that of the fabrics both treated with chlorine and heated on the other hand are determined as a percentage of the tear strength of the untreated fabrics.

The results are summarised in the following Table 3.

Table 3

| | Untreated | Liquor designation | | | | |
|---|---|---|---|---|---|---|
| | | A | B | C | D | E |
| constituents in g/l | | | | | | |
| Product according to Example 2 (P-content 13.8%) | | 227 | | | | |
| Product according to Example 3 (P-content 17.8%) | | | 176 | | | |
| Product according to Example 4 (P-content 17.8%) | | | | 175 | | |
| Product according to Example 5 (P-content 14.0%) | | | | | 224 | |
| Product according to Example 6 (P-content 15.8%) | | | | | | 198 |
| 2-amino-2-methyl-1-propanol-hydrochloride | | 40 | 40 | 40 | 40 | 40 |
| reaction product from 1 mole of 4-nonylphenol and 9 moles of ethylene oxide | | 2 | 2 | 2 | 2 | 2 |
| di-trimethylolmelamine | | 150 | 150 | 150 | 150 | 150 |
| hexamethylolmelaminepentamethyl ether-stearic acid-alkanolamide reaction product 30% | | 20/20 | 20 | 20 | 20 | |
| g of phosphorous per kg of fabric | | 25 | 25 | 25 | 25 | 25 |
| pH-value of the bath | | 6,8 | 6,8 | 6,8 | 6,8 | 6,8 |
| fixation degree in % | 74 | 81 | 88 | 84 | 81 | |
| flameproofness | | | | | | |
| BT = burning time in seconds | | | | | | |
| TL = tear length in cm. | | | | | | |
| after subsequent washing BT | burns | 0 | 0 | 0 | 0 | 0 |
| TL | | 12,5 | 13 | 12,5 | 11,5 | 11,5 |

Table 3-continued

| | Untreated | Liquor designation | | | | |
| --- | --- | --- | --- | --- | --- | --- |
| | | A | B | C | D | E |
| after 20 washes BT | burns | 0 | 0 | 0 | 0 | 0 |
| TL | | 12,5 | 12 | 10,5 | 11,5 | 11 |
| after 40 washes BT | burns | 0 | 0 | 0 | 0 | 0 |
| TL | | 14,5 | 12 | 11,5 | 12,5 | 11,5 |
| handle | | 1 | 1 | 1 | 1½ | 1 |
| scorch test subsequent tear strength chlorine-treated/untreated fabric % | 99,5 | 98,3 | 95,0 | 101,1 | 99,0 | |
| subsequent tear strength chlorine- and heat treated/untreated fabric % | 101,2 | 93,8 | 95,1 | 101,1 | 100,0 | 95,5 |

EXAMPLE 10

In a manner analogous to that described in Example 8, a cotton fabric is flameproofed with the liquor A of the composition given in the following Table 4 and then tested for its flameproofness.

The results are summarised in the following Table 4.

Table 4

| | Untreated | Treated with liquor A |
| --- | --- | --- |
| constituents in g/l | | |
| products according to Example 7 (P-content: 14.3%) | | 305 |
| di-trimethylolmelamine | | 150 |
| reaction product from 1 mole of 4-nonylphenol and 9 moles of ethylene oxide | | 2 |
| 2-amino-2-methyl-1-propanol-hydrochloride | | 40 |
| g of phosphorous per kg of fabric | | 35 |
| pH-value of the bath | | 6 |
| fixation degree in % | | 44 |
| flameproofness | | |
| BT = burning time in sec. | | |
| TL = tear length in cm. | | |
| before subsequent washing BT | burns | 0 |
| TL | | 8.5 |
| after subsequent washing BT | burns | 0 |
| TL | | 11.5 |
| after 1 wash BT | burns | 0 |
| TL | | 12.5 |

EXAMPLE 11

In a manner analogous to that given in Example 8, a fabric made from regenerated cellulose is flameproofed with the liquor A of the composition shown in the following Table 5; but the fabric is then only washed and afterwards re-washed.

The test for flameproofness is carried out as described in Example 8.

The results are summarised in the following Table 5.

Table 5

| | Untreated | Treated with liquor A |
| --- | --- | --- |
| constituents in g/l | | |
| product according to Example 8 (P-content: 14.3%) | | 305 |
| di-trimethylolmelamine | | 150 |
| reaction product from 1 mole of 4-nonylphenol and 9 moles of ethylene oxide | | 2 |
| 2-amino-2-methyl-1-propanol-hydrochloride | | 40 |
| g of phosphorous per kg of fabric | | 35 |
| pH-value of the bath | | 6 |
| fixation degree in % | | 60 |
| Flameproofness | | |
| BT — burning time in sec. | | |
| TL = tear length in cm. | | |
| before subsequent washing BT | burns | 0 |
| TL | | 8 |
| after subsequent washing BT | burns | 0 |
| TL | | 7 |
| after 1 wash BT | burns | 8 |
| TL | | 13.5 |

We claim:

1. A process for the flameproofing of organic fiber materials, which process comprises applying to these fiber materials (A) an amidophosphate reaction product which has been produced by reacting together at temperatures of 20° to 80° C. with or without acidic or basic catalysts (1) 1 or 2 moles of an amidophosphate of the formula $$\begin{array}{c} R_1-O \\ \phantom{R_1-O} \diagdown \phantom{O} \diagup O \\ \phantom{R_1-OO} P \\ \phantom{R_1-O} \diagup \phantom{O} \diagdown \\ R_1-O \phantom{OOO} NH_2 \end{array}$$

wherein $R_1$ is alkyl with 1 to 3 carbon atoms, alkenyl or halogenoalkyl with 2 or 3 carbon atoms or both $R_1$'s together are alkylene with 2 to 5 carbon atoms, (2) 1 mole of formaldehyde or an agent releasing formaldehyde, (3) an aliphatic diol with 2 to 6 carbon atoms, and-/or (4) an alkanol with 1 to 3 carbon atoms, and (B) optionally an aminoplast precondensate; drying the materials and then subjecting them to a treatment at elevated temperature above 100° C.

2. A process according to claim 1 which process comprises applying to the fiber materials as constituent (A) an amidophosphate reaction product which has been produced by reacting as constituent (1) an amidophosphate of the formula $$\begin{array}{c} R_2-O \\ \phantom{R_2-O} \diagdown \phantom{O} \diagup O \\ \phantom{R_2-OO} P \\ \phantom{R_2-O} \diagup \phantom{O} \diagdown \\ R_2-O \phantom{OOO} NH_2 \end{array}$$

wherein $R_2$ is alkyl with 1 to 3 carbon atoms, or both $R_2$'s togehter are alkylene with 2 to 5 carbon atoms.

3. A process according to claim 1 which process comprises applying to the fiber materials as constituent (A) an amidophosphate reaction product which has been produced by reacting as constituent (1) an amidophosphate of one of the formulae

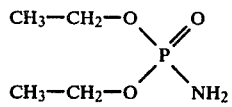

,

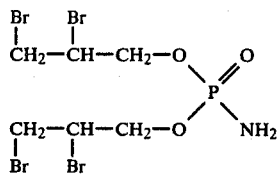

or

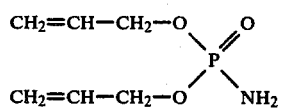

4. A process according to claim 1 which process comprises applying to the fiber materials as constituent (A) an amidophosphate reaction product which has been produced by reacting as constituent (2) an aqueous formaldehyde solution or paraformaldehyde.

5. A process according to claim 1 which process comprises applying to the fiber materials as constituent (A) an amidophosphate reaction product which has been produced by reacting as constituent (3) a diol of the formula

HO—$Q_1$—OH wherein $Q_1$ is unsubstituted alkylene with 1 to 6 carbon atoms, halogenated alkylene with 1 to 6 carbon atoms, unsubstituted alkylene with 2 to 6 carbon atoms and 1 or 2 oxygen atoms or 1 or 2 double or triple bonds, or halogenated alkylene with 2 to 6 carbon atoms and 1 or 2 oxygen atoms or 1 or 2 double or triple bonds.

6. A process according to claim 1 which process comprises applying to the fiber materials as constituent (A) an amidophosphate reaction product which has been produced by reacting as constituent (3) a diol of the formula

HO—$Q_2$—OH wherein $Q_2$ is unsubstituted alkylene with 1 to 6 carbon atoms, alkylene with 1 to 6 carbon atoms which is substituted with 2 to 4 chlorine or bromine atoms, unsubstituted alkylene with 2 to 6 carbon atoms and one double or triple bond, alkylene with 2 to 6 carbon atoms and one double or triple bond which is substituted with 2 to 4 chlorine or bromine atoms, unsubstituted alkylene with 4 to 6 carbon atoms and 2 oxygen atoms, 2 or 3 carbon atoms being between the oxygen atoms, or alkylene with 4 to 6 carbon atoms and 2 oxygen atoms which is substituted with 2 to 4 chlorine or bromine atoms, 2 or 3 carbon atoms being between the oxygen atoms.

7. A process according to claim 1 which process comprises applying to the fiber materials as constituent (A) an amidophosphate reaction product which has been produced by reacting as constituent (3) ethylene glycol, diethylene glycol or 1,2-propanmediol.

8. A process according to claim 1 which process comprises applying to the fiber materials as constituent (A) an amidophosphate reaction product which has been produced by reacting as constituent (4) ethanol or methanol.

9. A process according to claim 1 which process comprises applying to the fiber materials as optional constituent (B) an etherfied or unetherfied methylol melamine.

10. A process according to claim 1 which process comprises applying to the fiber materials as constituent (A) an amidophosphate reaction product which has been produced by reacting di- or trimethylol melamine.

11. A process according to claim 1 which process comprises drying the organic fiber materials at a temperature of up to 100° C. and subjecting them to a dry heat treatment at temperatures between 130° and 200° C.

12. A process according to claim 1 in which cellulose containing fiber materials are provided with a flameproofing finish.

* * * * *